(12) United States Patent
Ferrari et al.

(10) Patent No.: US 9,802,906 B1
(45) Date of Patent: Oct. 31, 2017

(54) PROCESS FOR THE PREPARATION OF TOLTRAZURIL AND AN INTERMEDIATE USEFUL FOR ITS PREPARATION

(71) Applicant: ERREGIERRE S.p.A., San Paolo D'Argon (IT)

(72) Inventors: Massimo Ferrari, Cenate Sotto (IT); Daniele De Zani, Roncello (IT); Matteo Bonaldi, Sorisole (IT)

(73) Assignee: ERREGIERRE S.P.A., San Paolo D'Argon (IT)

( * ) Notice: Subject to any disclaimer, the term of this patent is extended or adjusted under 35 U.S.C. 154(b) by 0 days.

(21) Appl. No.: 15/480,565

(22) Filed: Apr. 6, 2017

(30) Foreign Application Priority Data

May 11, 2016 (IT) .................... 102016000037106

(51) Int. Cl.
*C07D 251/30* (2006.01)
*C07C 275/60* (2006.01)
*C07C 271/66* (2006.01)

(52) U.S. Cl.
CPC .......... *C07D 251/30* (2013.01); *C07C 271/66* (2013.01); *C07C 275/60* (2013.01)

(58) Field of Classification Search
CPC ............................ C07D 251/30; C07C 275/60
USPC .................................... 544/221; 564/44, 418
See application file for complete search history.

(56) References Cited

U.S. PATENT DOCUMENTS 4,874,860 A    10/1989   Gallenkamp et al.
4,898,979 A    2/1990    Gallenkamp et al.

FOREIGN PATENT DOCUMENTS

CN    102936227 A    2/2013

OTHER PUBLICATIONS

International Search Report and Written Opinion of Italian Application No. IT UA20162789.

*Primary Examiner* — Vankataraman Balasubramanian
(74) *Attorney, Agent, or Firm* — Silvia Salvadori, P.C.; Silvia Salvadori

(57) ABSTRACT

Disclosed is a process for the preparation of toltrazuril of formula (I) via the intermediate N-methyl-N'-[3-methyl-4-[4-[(trifluoromethyl)thio]phenoxy]phenyl] imidodicarbonic diamide of formula (III)

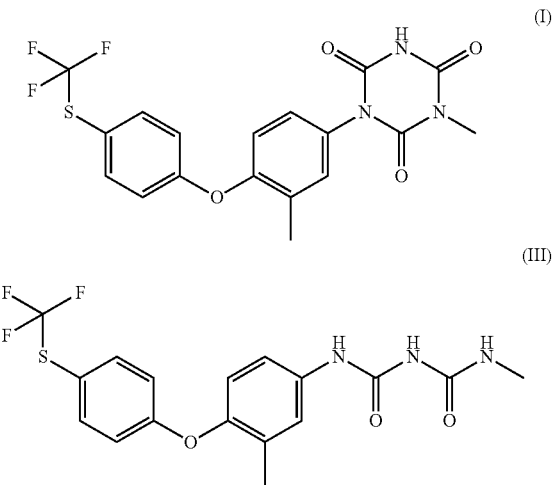

wherein intermediate (III) is obtained via a novel intermediate without the use of potentially hazardous reagents or potentially unstable intermediates.

5 Claims, No Drawings

PROCESS FOR THE PREPARATION OF TOLTRAZURIL AND AN INTERMEDIATE USEFUL FOR ITS PREPARATION

This U.S. Non-Provisional Application claims priority to and the benefit from Italian Patent Application No. 102016000037106 filed on Apr. 11, 2016, the content of which is incorporated herein by reference in its entirety.

The invention relates to a process for the preparation of toltrazuril and an intermediate for its preparation.

BACKGROUND TO THE INVENTION

Toltrazuril, (1-methyl-3-[3-methyl-4-[4-(trifluoromethylthio)phenoxy]-phenyl]-1,3,5-triazin-2,4,6(1H,3H,5H)-trione) of formula (I), is an agent widely used in the veterinary field for the prevention and treatment of coccidiosis, particularly in poultry and pigs.

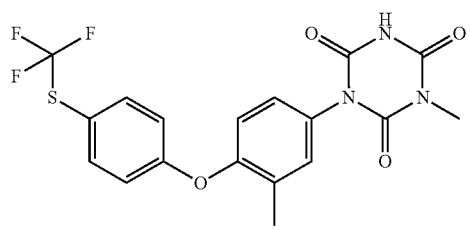

(I)

The preparation of toltrazuril is reported in U.S. Pat. No. 3,966,725 and U.S. Pat. No. 4,219,552, which describe a general process for the preparation of various 1-(4-phenoxyphenyl)-1,3,5-triazin-2,4,6 1H,3H,5H)-triones. In the case of toltrazuril, the process involves reacting 1-[3-methyl-4-[4 (trifluoromethylthio)phenoxy]phenyl]-3-methylurea of formula (II) with chlorocarbonyl isocyanate, as reported in Scheme 1.

Scheme 1

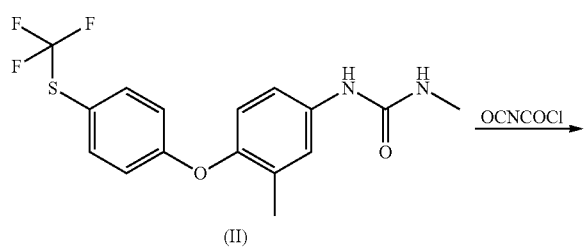

U.S. Pat. No. 4,874,860 and DE 4239000 disclose the preparation of toltrazuril by cyclisation of N-methyl-N'-[3-methyl-4-[4-[(trifluoromethyl)thio]phenoxy]-phenyl]imidodicarbonic diamide of formula (III), commonly known as biuret toltrazuril intermediate, with diethyl carbonate in the presence of sodium methylate, as reported in Scheme 2.

Scheme 2

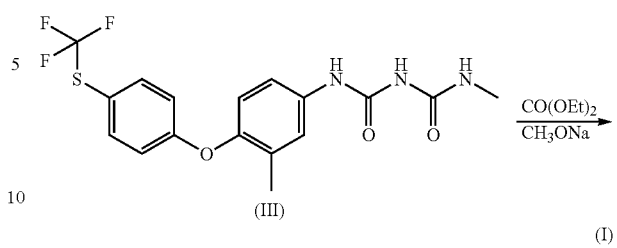

The biuret intermediate (III) is obtained in turn by reacting the aniline intermediate 3-methyl-4-[4-(trifluoromethylthio)phenoxy]benzenamine (IV) with phosgene to give the corresponding isocyanate (V), which is then reacted with N-methylurea, as reported in Scheme 3.

Scheme 3

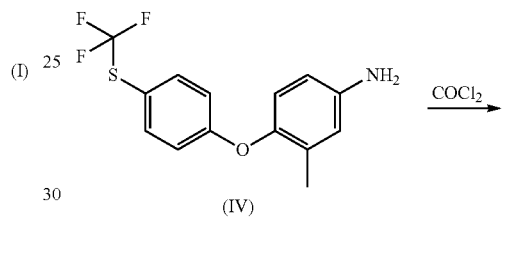

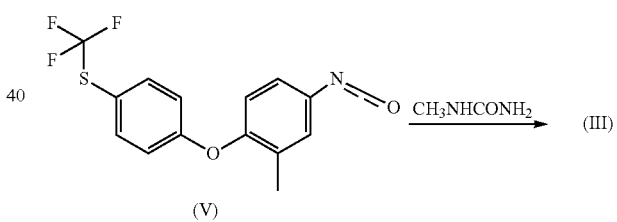

CN 101265236 discloses the reaction of isocyanate (V) with intermediate (IV) and triphosgene instead of phosgene, while CN102108067 describes the reaction between intermediate (IV) and BOC-anhydride/DMAP.

CN 101108831 describes the preparation of toltrazuril wherein the ureide intermediate (II) is obtained by treating aniline (IV) with triphosgene to give isocyanate (V), which is then reacted with methylamine, as reported in Scheme 4.

Scheme 4

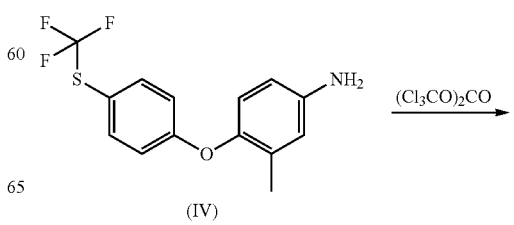

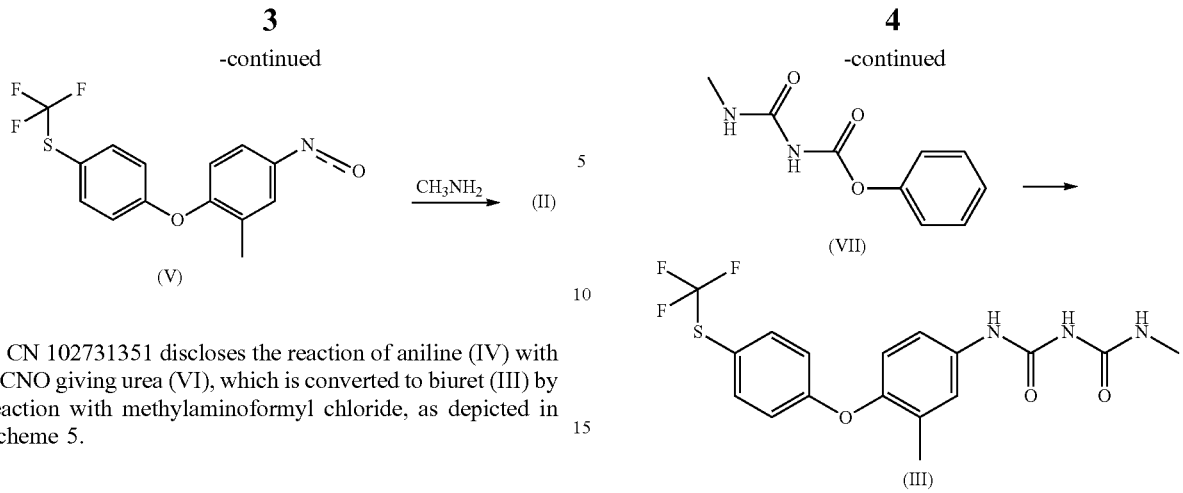

CN 102731351 discloses the reaction of aniline (IV) with KCNO giving urea (VI), which is converted to biuret (III) by reaction with methylaminoformyl chloride, as depicted in Scheme 5.

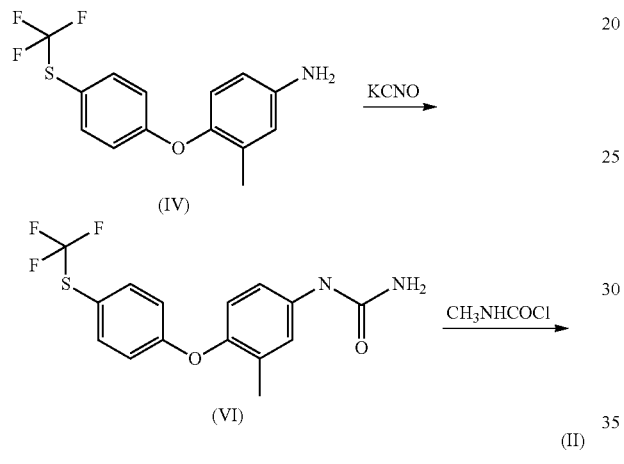

The synthesis routes of toltrazuril via intermediate (III) reported so far therefore involve the use of potentially hazardous reagents like phosgene and triphosgene and/or a step involving unstable intermediates like isocyanates.

DESCRIPTION OF THE INVENTION

The object of the present invention is a process for the preparation of toltrazuril which comprises:

a) reaction of (methylaminocarbonyl)carbamic acid phenyl ester of formula (VII) with 3-methyl-4-[4-(trifluoromethylthio)phenoxy]benzenamine of formula (IV) to give N-methyl-N'-[3-methyl-4-[4-[(trifluoromethyl)thio]phenoxy]phenyl]-imidodicarbonic diamide of formula (III), as depicted in Scheme 6 below

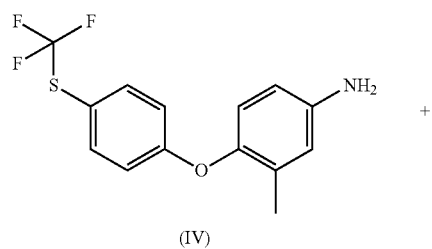

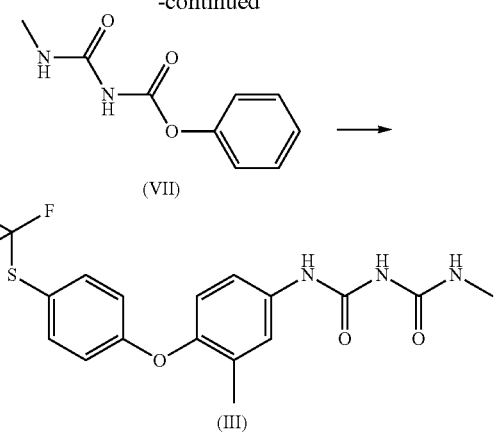

Scheme 6 b) cyclisation of compound (III) to give toltrazuril.

(Methylaminocarbonyl)carbamic acid phenyl ester (VII) is a novel compound that is a further object of the invention. Said compound can be obtained by reacting phenyl chloroformate of formula (VIII) with N-methylurea, as reported in Scheme 7.

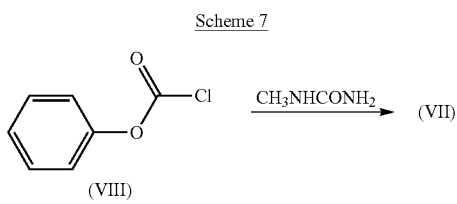

DETAILED DESCRIPTION OF THE INVENTION

The reaction between aniline (IV) and (methylaminocarbonyl)carbamic acid phenyl ester (VII) is carried out using equimolar amounts of the reagents or a slight molar excess (5-20%), preferably 5-10%, of (VII), at a temperature ranging from 20° C. to 90° C., preferably from 60° C. to 80° C. The reaction is carried out in an organic solvent selected from N,N-dimethylformamide, N,N-dimethylacetamide and ethyl acetate, preferably N,N-dimethylacetamide, for a time ranging from 6 to 18 hours, preferably for 12 hours.

The phenylcarbamic intermediate (VII) is obtained by reacting phenyl chloroformate (VIII) with N-methylurea in a solvent selected from methylene chloride, ethyl acetate, acetone, N,N-dimethylformamide and toluene, preferably toluene, in the presence of a base selected from triethylamine and pyridine, preferably pyridine. The reaction is conducted at a temperature ranging from 40° C. to 60° C., preferably from 50° C. to 60° C.

3-Methyl-4-[4-(trifluoromethylthio)phenoxy]benzenamine (IV) is a known compound, which can be obtained by condensation between 4-(trifluoromethylthio)-phenol (IX) and 2-chloro-5-nitrotoluene (X) in the presence of a base, followed by reduction of the resulting nitro derivative (XI) with hydrogen and palladium-on-carbon catalysis, as disclosed, for example, in U.S. Pat. No. 4,219,552 and summarised in Scheme 8.

Scheme 8

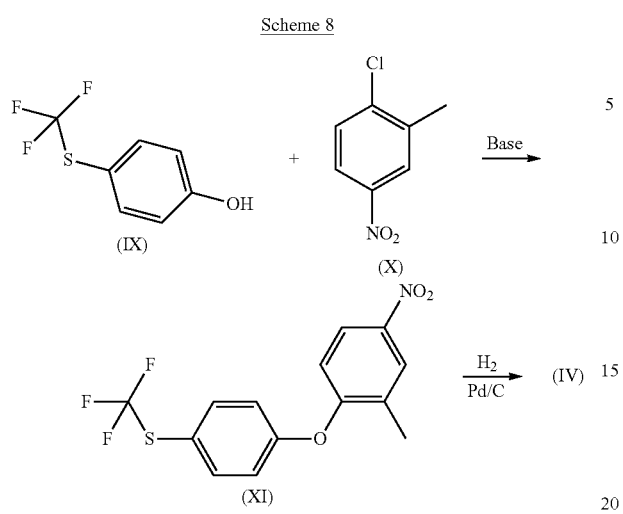

The biuret intermediate (III) can be converted to toltrazuril by known procedures, for example by reaction with diethyl carbonate in the presence of a base, as described in U.S. Pat. No. 4,874,860.

The process according to the invention produces biuret intermediate (III) with no need to use hazardous reagents such as those described in the literature to date for its preparation, and also avoids the step involving unstable intermediates considered potentially hazardous, such as isocyanates.

The invention will now be illustrated by the following examples.

Example 1—Preparation of [(Methylamino)Carbonyl]Carbamic Acid Phenyl Ester 20.5 Kg of N-methylurea (276.7 moles), 61.5 Kg of toluene and 26.3 Kg of pyridine (332.5 moles) are loaded into a reactor. The suspension is heated to 40-60° C. and, maintaining said temperature by cooling, 47.6 Kg of phenyl chloroformate (304.25 moles) is poured into it. The reaction is maintained at 50-60° C. for one hour, after which 51.3 Kg of methanol is added. The suspension is cooled to 0-10° C., after which the solid is recovered by filtration, washed with 30.8 Kg of methanol, and dried at 60-70° C. 45.1 Kg of [(methylamino)carbonyl]carbamic acid phenyl ester (232.4 moles) is obtained. HPLC purity=99%. Yield: 84%.

Example 2 Preparation of N-Methyl-N'-p-Methyl-4-[4-[(trifluoromethyl)thio]phenoxy]phenyl]imidodicarbonic diamide 64.9 Kg of 3-methyl-4-[4-[(trifluoromethylthio)]phenoxy]benzenamine (216.82 moles), 64.9 Kg of N,N-dimethylacetamide and 45.1 Kg of [(methylamino)carbonyl] carbamic acid phenyl ester (232.2 moles) are loaded into a reactor. The mass is heated at 60-80° C. for 12 hours, after which 130 Kg of toluene, 130 Kg of water and 31.8 Kg of sodium hydrate (in 30% w/w aqueous solution) are added. The lower aqueous phase is separated and eliminated, and 64.9 Kg of distilled water is added to the organic phase. The mixture is cooled to 30-45° C. (crystallisation takes place), then cooled to 0-5° C. and filtered washing first with 64.9 Kg of toluene and then with 64.9 Kg of distilled water. The resulting product is dried at 60-70° C. 74.5 Kg of N-methyl-N'-[3-methyl-4-[4-[(trifluoromethyl)thio]phenoxy]phenyl]-imidodicarbonic diamide is obtained. HPLC purity=99%. Yield 86%.

The invention claimed is:

1. A process for the preparation of toltrazuril of formula (I)

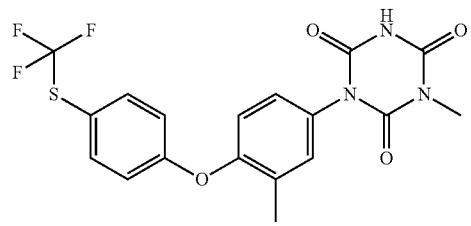

which comprises:
a) reacting (methylaminocarbonyl)carbamic acid phenyl ester of formula (VII)

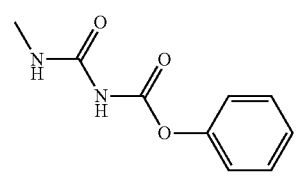

with 3-methyl-4-[4-(trifluoromethylthio)phenoxy]benzenamine of formula (IV)

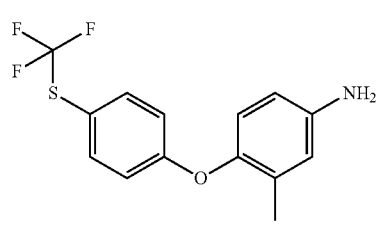

to give the compound of formula (III)

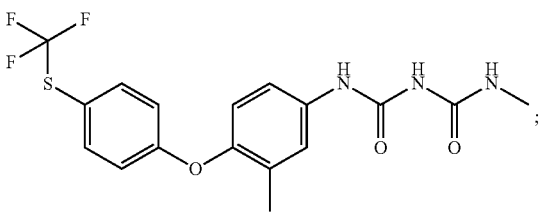

and
b) cyclizing the compound of formula (III) to give toltrazuril.

2. The process of claim 1 wherein the reaction between (IV) and (VII) is carried out at a temperature ranging from 60° C. to 80° C. in an organic solvent selected from N,N-dimethylformamide, N,N-dimethylacetamide and ethyl acetate, for a time ranging from 6 to 18 hours.

3. The process of claim 1, wherein the compound of formula (VII) is obtained reacting phenyl chloroformate with N-methylurea.

4. The process of claim 3, wherein the reaction between phenyl chloroformate and N-methylurea is carried out in a solvent selected from methylene chloride, ethyl acetate, acetone, N,N-dimethylformamide and toluene in the presence of a base selected from triethylamine and pyridine, wherein said reaction is performed at a temperature ranging from 40° C. to 60° C.

5. The compound of formula (VII)

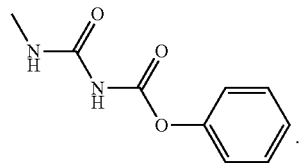
(VII)

.

* * * * *